(12) United States Patent (10) Patent No.: US 7,448,515 B2
Ramirez-Delgado (45) Date of Patent: Nov. 11, 2008

(54) AUTOMATIC MACHINE FOR DOSING WATER AND DENTAL ALGINATE

(76) Inventor: Roberto Alfredo Ramirez-Delgado, Industria del Plastico No. 2113, Zapopan Industrial Norte, 45132 Zapopan, Jalisco (MX)

( * ) Notice: Subject to any disclaimer, the term of this patent is extended or adjusted under 35 U.S.C. 154(b) by 274 days.

(21) Appl. No.: 11/390,489

(22) Filed: Mar. 28, 2006

(65) Prior Publication Data

US 2006/0231570 A1    Oct. 19, 2006

Related U.S. Application Data

(63) Continuation-in-part of application No. 11/105,572, filed on Apr. 14, 2005.

(51) Int. Cl.
*B67D 5/08* (2006.01)

(52) U.S. Cl. .............................. 222/52; 222/61; 222/63; 222/64; 222/129; 222/135; 222/258; 222/333; 222/413

(58) Field of Classification Search .................... 222/52, 222/61, 63–64, 129, 135, 158–159, 161–162, 222/226–227, 261–263, 333–334, 258, 643, 222/631–632, 196, 198, 236, 241, 410–413, 222/233, 238; 433/27, 28
See application file for complete search history.

(56) References Cited

U.S. PATENT DOCUMENTS

| 4,490,046 | A | * | 12/1984 | Guibert ..................... 366/76.4 |
| 4,691,846 | A | * | 9/1987 | Cordell et al. .............. 222/198 |
| 5,325,638 | A | * | 7/1994 | Lynn ............................ 451/39 |
| 6,120,567 | A | * | 9/2000 | Cordell et al. ............ 48/197 R |
| 6,145,709 | A | * | 11/2000 | Hogan et al. ................. 222/278 |
| 6,309,570 | B1 | * | 10/2001 | Fellabaum ................. 264/40.1 |
| 2006/0231573 | A1 | * | 10/2006 | Ramirez-Delgado ......... 222/64 |

* cited by examiner

*Primary Examiner*—Frederick C. Nicolas
(74) *Attorney, Agent, or Firm*—Browdy and Neimark, P.L.L.C.

(57) ABSTRACT

An automatic machine for dosing water and dental alginate is disclosed. The machine comprises a water container and a dental alginate container. In the automatic machine, a predetermined amount of each of those substances is transported from its respective container to a dosing point. During operation of the automatic machine, dental alginate is moved inside the alginate container with the purpose of homogenously distribute the alginate and bringing down residues of alginate adhered to the internal walls of the alginate container. In addition, the automatic machine comprises a control unit with a memory that stores dosing programs, this memory can be programmed in order to handle dental alginate supplied by different manufactures.

13 Claims, 9 Drawing Sheets

FIG. 11

AUTOMATIC MACHINE FOR DOSING WATER AND DENTAL ALGINATE

CROSS REFERENCE TO RELATED APPLICATION

This application is a continuation-in-part of U.S. application Ser. No. 11/105,572, filed on Apr. 14, 2005.

TECHNICAL FIELD

This invention relates to the techniques used to design apparatus and equipment for dental purposes, and more specifically, relates to an automatic machine for dosing water and dental alginate.

BACKGROUND OF THE INVENTION

In order to take dental impressions, it is well known that dentists use an alginate gel poured into a mold that is positioned around the teeth of a patient. Once the gel has solidified into the mold, the same is extracted from the mouth of the patient, thus obtaining the desired dental impression.

With regard to the above, alginate gel is obtained from a mixture of water and alginate powder. It is important mentioning that said powder is very fine and is obtained from marine algae as its main raw material. When dental alginate is mixed with water, a gelification reaction occurs between such substances.

When a dentist or his assistant is preparing a mixture of water and alginate, he must be careful of exactly measuring predetermined amounts of such ingredients in order to form a gel having the desired consistency, which allows the dentist to work easily with the gel. Therefore, alginate producers recommend and indicate in their products the exact amounts of water and alginate to be measured in order to prepare adequate mixtures. In fact, most of the alginate producers include in their packages two measuring devices, one for alginate and one for water, with the purpose of measuring such required amounts. The measuring devices are containers, spoons, etc., most of them having printed marks that indicate the dentist the amount of water or alginate that is measured.

Moreover, some alginate producers often include kits for preparing mixtures; one of said kits is disclosed in U.S. Pat. No. 5,709,467, incorporated herein by reference. Particularly, the invention of this patent is a mixing pouch, in which water and alginate are mixed by hand. In a preferred embodiment of the invention disclosed in said patent, a predetermined amount of alginate is previously included into the pouch, therefore a dentist only have to add water into the pouch and mix the content. However, this document does not mention how to exactly measure the required amounts of alginate. In addition, if a package of alginate is provided with a set of pouches, the volume of the package will be increased.

Measuring water and alginate is not an easy and fast work for dentists, since there are some cares that must be taken, for example, due to the tendency of alginate powder to form lumps, the alginate package must be shaken prior to extract the alginate with the corresponding measuring device. Alginate has hydrophilic properties, therefore, it is recommended to store the packages of alginate in dry places in order to maintain the properties of this substance.

With regard to the above, if a dentist uses lumps of alginate, it is very probable that he will measure an incorrect amount of alginate and the resulting mixture will have a poor performance for taking dental impressions. This problem also occurs when a dentist uses amounts of water distinct to those recommended by the alginate producer.

In addition, when dentists handle alginate powder, there are cleaning problems on the working area, inasmuch as alginate powder is very volatile and tends to float in the air. This problem is more frequent when an excess of alginate is extracted from the package using such measuring devices, inasmuch as some part of the excess will be inevitably deposited on the working area when the dentist tries to return the excess to the package. On the other hand, dentists must be careful of avoiding alginate to be contaminated by dust or substances contained in the air when a package is opened.

From the foregoing, it can be observed that a dentist or his assistant has to spend much time in measuring the required amounts of water and alginate and they have to adequately handle alginate. In the prior art, there is a lack of devices or machines that automatic measuring the substances used for taking dental impressions. In other words, nowadays, there is not a machine for dosing water and alginate, which covers all the dentist requirements in this measuring and handling activity.

SUMMARY OF THE INVENTION

A solution has been developed to avoid the problems of measuring and dosing water and alginate, which are used in a mixture for taking dental impressions; this solution is particularly related to an automatic machine for dosing water and dental alginate according to predetermined amounts. The automatic machine of the present invention comprises: a water container in which water is stored; means for flowing water from said water container to a water dosing point; an alginate container in which dental alginate is stored; means for transporting dental alginate from the bottom of said alginate container to an alginate dosing point which is outside of said alginate container; means for distributing dental alginate over said transporting means; and, a control unit being electrically connected to: i) said flowing means, ii) said transporting means, and iii) said distributing means.

This combination of elements, which together form the automatic machine for dosing water and dental alginate of the present invention, allow a user to obtain water and dental alginate according to predetermined amounts, which are exactly measured by the machine. More particularly, when the user wishes to obtain water and dental alginate from the automatic machine, he only has to operate said control unit, which, in turn, operates said flowing means in order to dose a predetermined amount of water from said water container to the water dosing point; then, said control unit operates said distributing means in order to move dental alginate inside said alginate container and homogenously distribute dental alginate over said transporting means; which are also operated by said control unit in order to carry a predetermined amount of dental alginate from the bottom of said alginate container to the alginate dosing point.

Once the predetermined amount of alginate has been dosed, said control unit changes the operating direction of said transporting means in order to return any alginate amount remaining in said transporting means to said alginate container. Preferably, said transporting means and said distributing means operate at the same time.

In a first preferred embodiment, the transporting means comprises an arrangement of a helical worm located inside the alginate container and having a portion running outside the alginate container; a tube for housing the portion of the helical worm running outside the alginate container; and, means for rotating the helical worm inside the alginate container and the tube, so that, when the helical worm rotates, an amount of dental alginate is carried from the alginate container to the alginate dosing point.

On the other hand, the distributing means used in the automatic machine comprises: a first rotary roller having a first plurality of radially protruding extensions, the first roller is mounted inside said alginate container; a second rotary roller having a second plurality of radially protruding extensions, the second roller is also mounted inside said alginate container and is laterally separated from the first rotary roller, wherein the second rotary roller rotates in opposite direction with respect to the first rotary roller; a double ribbon worm mounted inside the alginate container and centrally located therein; the double ribbon worm being disposed between and under the first and second rotary rollers; and, means for rotating the double ribbon worm as well as the first and second rotary rollers.

Therefore, as the first and second rollers rotate, the extensions thereof move dental alginate to the center and towards the bottom of said alginate container, where dental alginate is received by the double ribbon worm, which homogenously distributes dental alginate over said transporting means. The extensions of the first and second rotary rollers destroy any lump of alginate inside the alginate container, if any.

The control unit of the machine includes a memory that stores dosing programs, which may be selected by the user using keys included in said control unit. In a preferred embodiment of the invention, the memory is programmable. This feature allows the user to work with dental alginate supplied by different manufactures, more specifically, the user can modify the amount of water to be dosed by the machine according to the specific properties of dental alginate that is inside the alginate container.

In an alternative embodiment of the present invention, the automatic machine further comprises: a first sensor associated to said alginate container and being in electrical connection with said control unit, the first sensor generates a first signal which is transmitted to said control unit, which, in turn, indicates the user the alginate powder amount available inside said alginate container; and, a second sensor associated to the water container and being in electrical connection with said control unit, the second sensor generates a second signal which is transmitted to said control unit, which, in turn, indicates the user the water amount available in said water container. If the level of water or dental alginate is lower than a minimum level, the control unit emits a visual or sound alarm.

In one aspect of the invention, the water container is pressurized and the distributing means are substituted by means for vibrating the alginate container. Preferably, the vibrating means are a pair of vibrating motors being in contact with the external surface of the bottom of said alginate container. The vibrating means moves dental alginate inside the alginate container; this movement has the purpose of conducting dental alginate to the bottom of this container, where alginate is received by the transporting means. Furthermore, the vibrating motion has the objective of bringing down residues of alginate adhered to the internal walls of the alginate container, if any.

In addition, the alginate container has the form of a hopper and it is made of polyethylene, this polymer avoids alginate to be adhered on the internal walls of the alginate container.

As it can be observed from the foregoing, it is an object of the present invention to provide an automatic machine for dosing water and dental alginate, wherein the dosed amounts of these substances are exactly measured by the machine.

Another object of the present invention is to provide an automatic machine for dosing water and dental alginate, which allow dentists to save time in the whole process of obtaining a dental impression.

Yet, it is an object of the present invention to provide an automatic machine for dosing water and dental alginate, wherein dental alginate is stored and dosed in optimal conditions.

BRIEF DESCRIPTION OF THE DRAWINGS

The novel aspects that are considered characteristic of the present invention are particularly set forth in the appended claims. The invention itself, however, both as to its structure and to its method of operation, together with additional objects and advantages thereof, will best be understood from the following description of preferred embodiments, when read in relation to the appended drawings, in which:

DETAILED DESCRIPTION OF THE INVENTION

Figure 1:
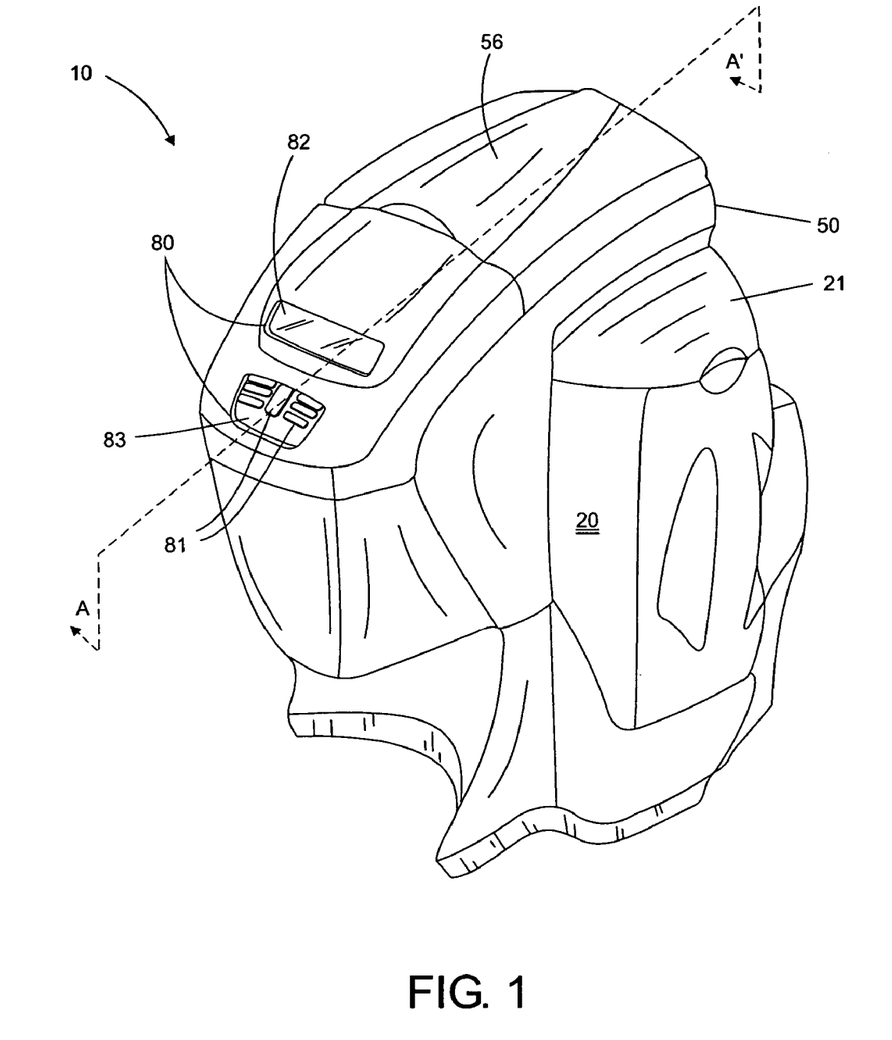
FIG. 1 is a perspective view of an automatic machine for dosing water and dental alginate, which is built according to a first preferred embodiment of the present invention.
Figure 2:
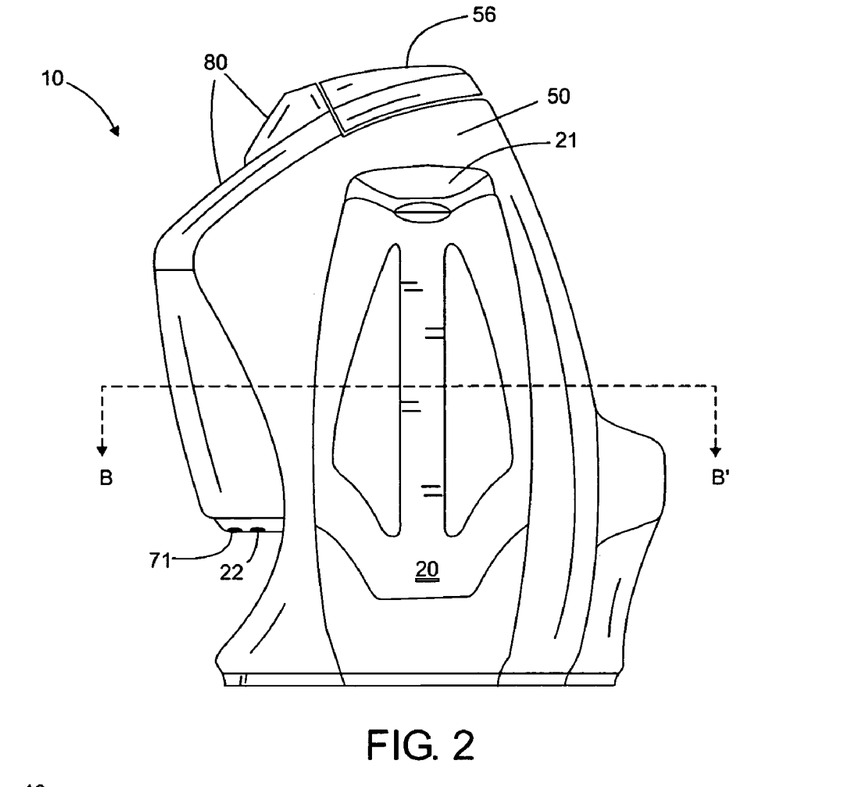
FIG. 2 is a side view of the automatic machine for dosing water and dental alginate of FIG. 1.
Figure 3:
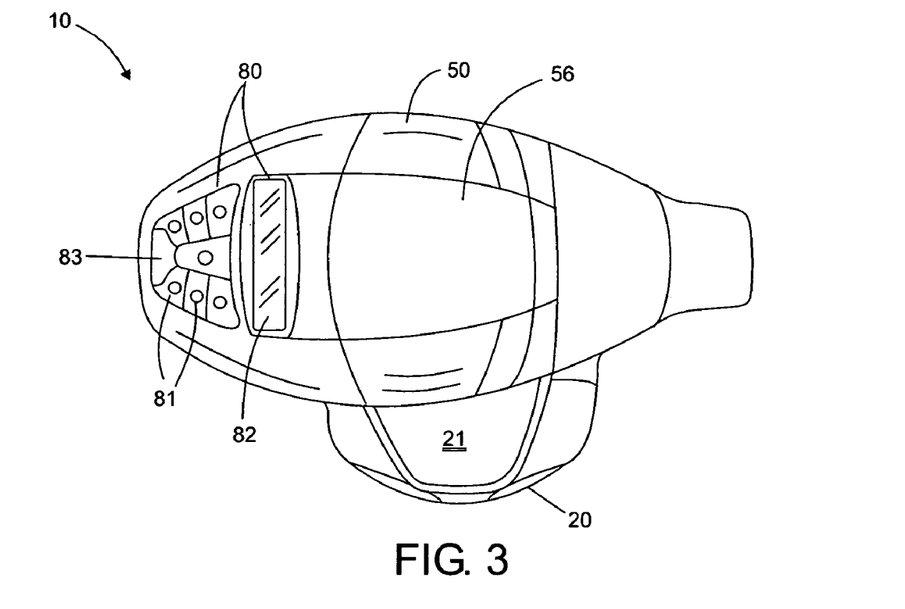
FIG. 3 is a top plan view of the automatic machine for dosing water and dental alginate of FIG. 1.

With specific reference to FIGS. 1 to 3 of the appended drawings, these show some external views of an automatic machine for dosing water and dental alginate 10, built in accordance with the principles of a first preferred embodiment of this invention, which should be considered as illustrative but not restrictive thereof. The automatic machine 10 of the first preferred embodiment comprises a water container 20, in which water is stored, this container 20 includes a lid 21, which can be removed o lifted in order to add water inside the water container 20 when the level of this liquid is lower than a minimum level. The automatic machine 10 also has means for flowing water from the container 20 to a water dosing point 22 (shown in FIG. 2); the flowing means used in this preferred embodiment will be described and explained later.

In FIGS. 1-3, it can also be observed an alginate container 50, in which dental alginate powder is stored. It is worth mentioning that the alginate container 50 is preferably made of polyethylene, this polymer avoids dental alginate to be adhered on the internal walls of the alginate container 50, therefore, old alginate is never kept inside the alginate container 50, which can store from about 1 pound (0.454 kg) to about 7 pounds (3.18 kg) of dental alginate, more preferably, it may store about 5 pounds (2.28 kg), this volume of the alginate container 50 allows a dentist to work for several weeks without refilling the alginate container 50. Refilling of the alginate container 50 is done lifting a lid 56 located at the upper part of the alginate container 50, which, inside the machine, has the form of a hopper with a "U" shaped bottom in cross section. The automatic machine 10 also has means for transporting dental alginate from the alginate container 50 to an alginate dosing point 71 (FIG. 2); the transporting means used in this first preferred embodiment will be disclosed later. Preferably, the alginate dosing point 71 and the water dosing point 22 are disposed one next to the other, whereby a dentist can receive both substances in a vessel and mix them.

On the other hand, the automatic machine 10 illustrated in FIGS. 1-3 also includes a control unit 80, which comprises a memory which stores dosing programs, each of them corresponding to a specific ratio between the amounts of water and dental alginate to be dosed. The control unit 80 has a control panel 83 having a plurality of keys 81, each of said keys 81 corresponds to a specific dosing program that the user may select. Finally, the control unit 80 includes a display 82, which is in electrical connection to the keys 81 and the memory, the display 82 shows the user the specific dosing program being performed by the automatic machine 10.

Figure 4:
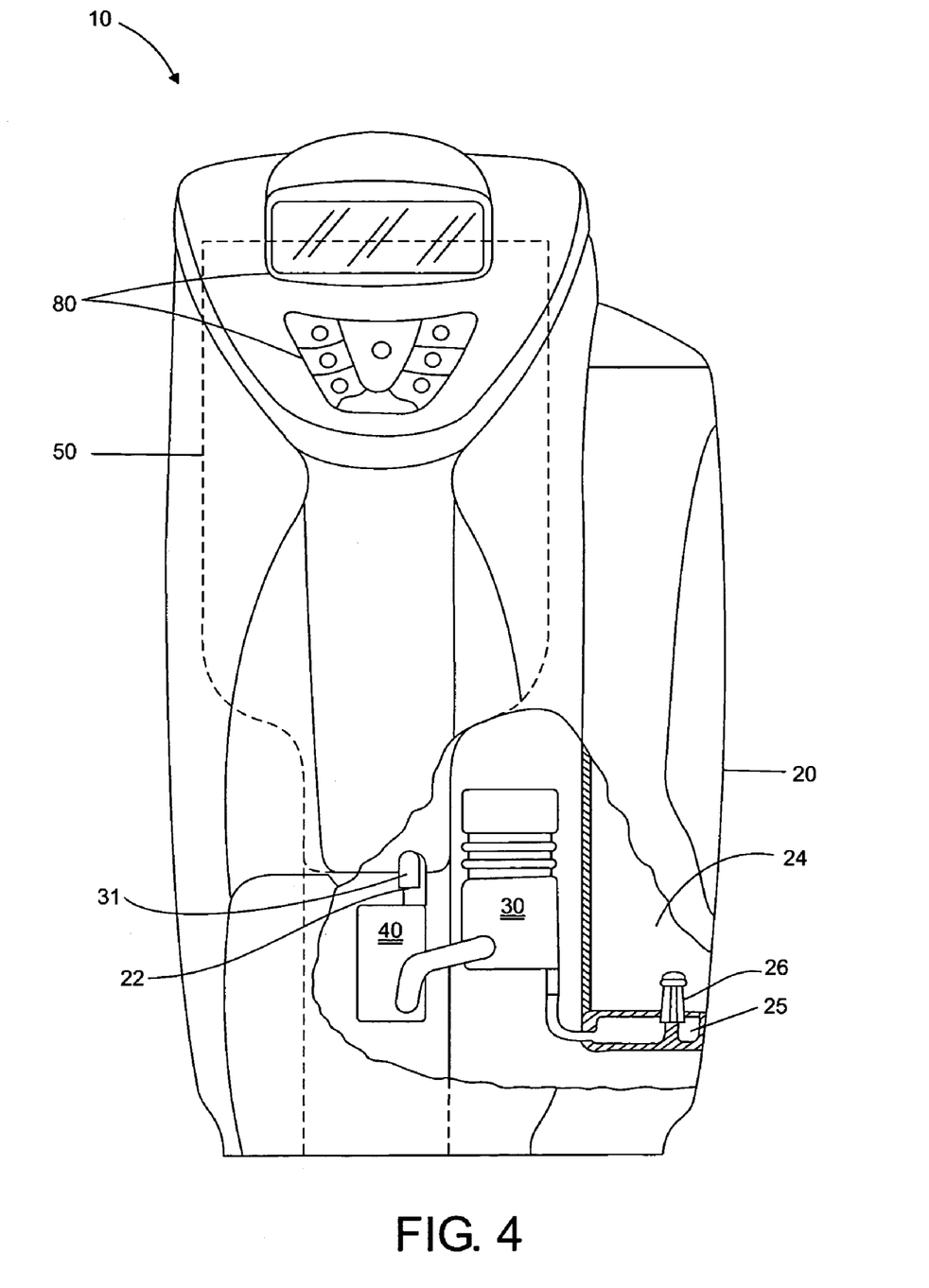
FIG. 4 is a fragmentary front view of the machine illustrated in FIG. 1, from which a part has been removed in order to show the elements used for dosing water.
Figure 5:
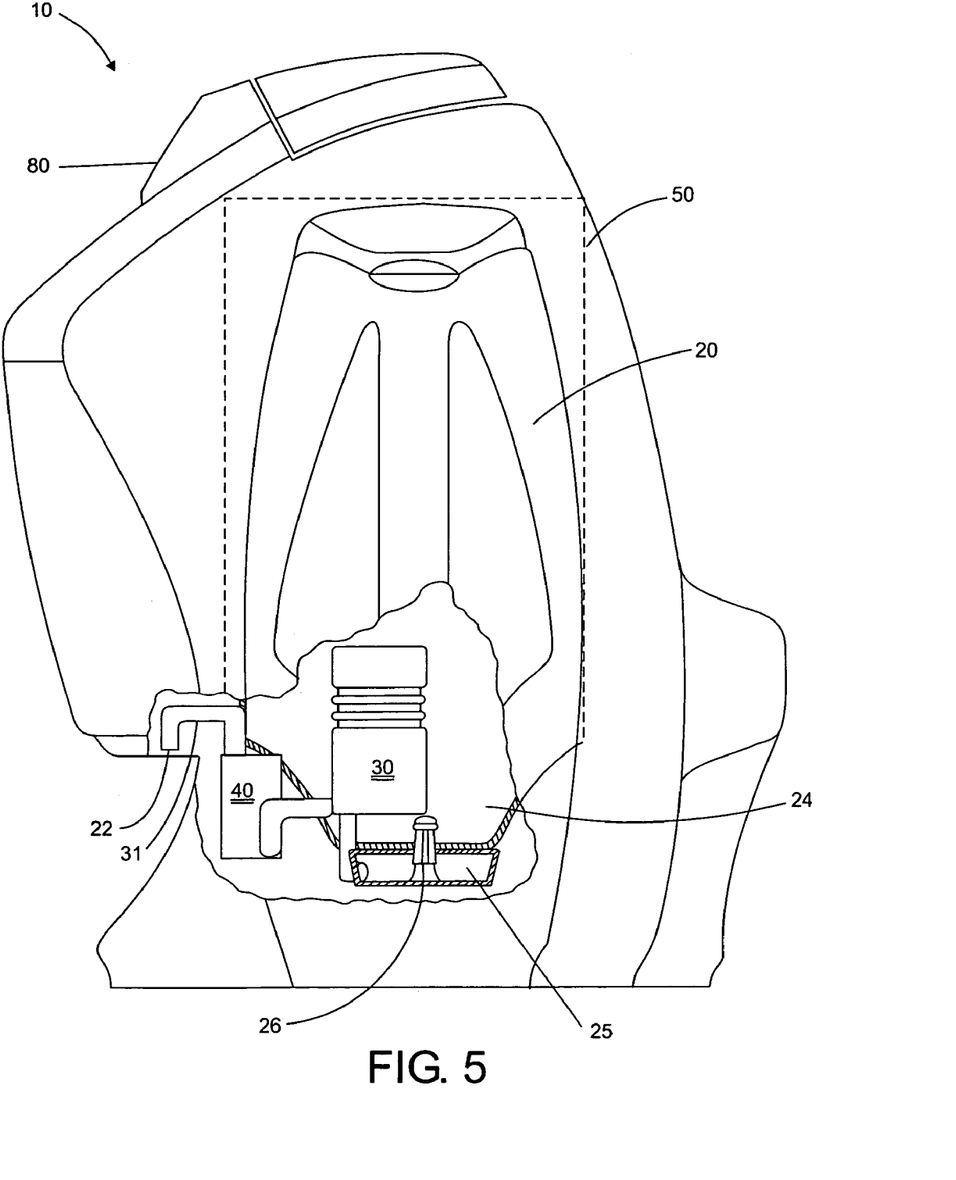
FIG. 5, is a fragmentary lateral view of the machine illustrated in FIG. 1, from which a part has been removed in order to show the elements used for dosing water.

Now, reference is made to FIGS. 4 and 5 in order to describe the flowing means that allow water to flow from the water container 20 to the water dosing point 22. The flowing means for this first preferred embodiment comprises a pump 30 in flow connection with said water container 20; and, a valve 40 in flow connection with said pump 30; whereby, water can flow from the water container 20 to the water dosing point 22 through the pump 30 and the valve 40 when the control unit 80 is in operation. In a specific embodiment of the invention, the valve 40 is an electrovalve having a hose 31 connected at the output of the valve 40; the dosing point of water 22 is the free end of the hose 31. Both the pump 30 and the valve 40 are calibrated is such a way that only the water amount required for preparing the desired mixture is dosed.

The water container 20 has a volume of about 0.5 liters to about 3 liters, preferably, 1.5 liters, and is divided in a superior chamber 24 and an inferior chamber 25, of which, the superior chamber 24 occupies most of the volume in the water container 20. On the other hand, the inferior chamber 25 always keeps water in order to maintain a positive pressure in the pump 30 for its correct operation. In the water container 20, this liquid passes from the superior chamber 24 to the inferior chamber 25 through a security valve 26, which prevents backflow of water from the pump 30 to the superior chamber 24. In FIGS. 4 and 5, dashed lines are used in order to show the contour of the alginate container 50 inside the automatic machine 10.

Figure 6:
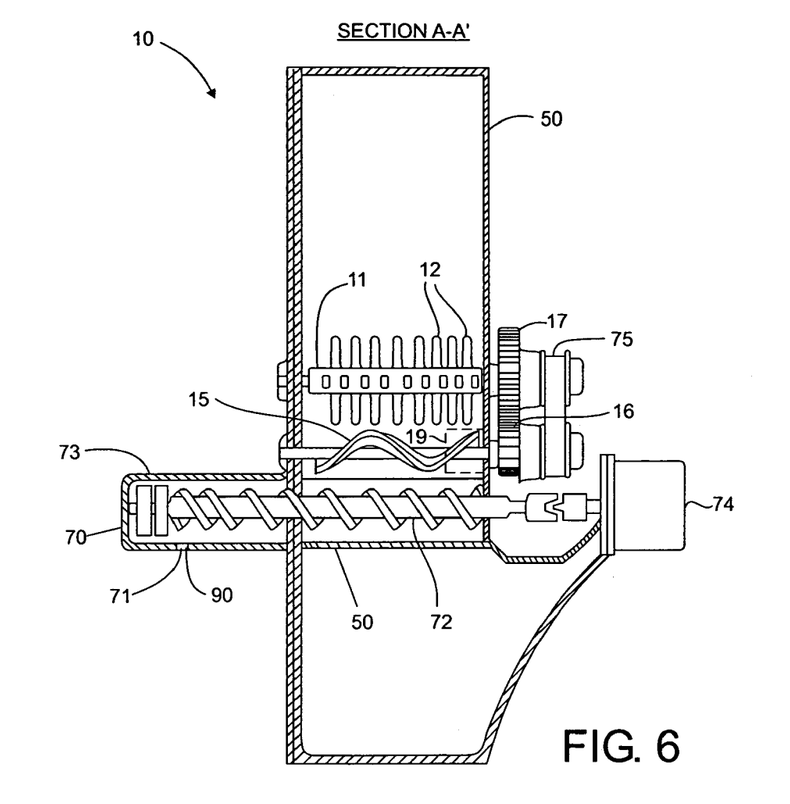
FIG. 6 is a cross section view of the machine taken along line A-A' of FIG. 1, from which a part has been removed in order to show the elements used for dosing dental alginate.
Figure 7:
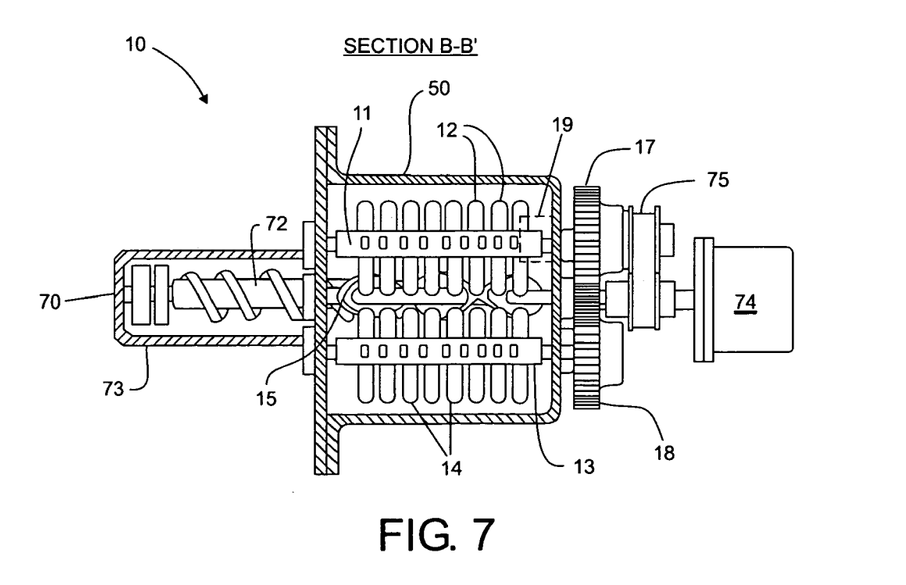
FIG. 7 is a top plan view of a cross-section taken along line B-B of FIG. 3, wherein a part of the automatic machine has been removed in order to show the elements used for dosing dental alginate.

Now, reference is made to FIGS. 6 and 7 in order to describe how dental alginate is moved inside the alginate container 50 and how dental alginate is transported from there to the alginate dosing point 71, where a dentist can receive this substance.

The transporting means, used in the first preferred embodiment of the present invention, comprises: a helical worm 72 horizontally disposed along the bottom of said alginate container 50, one end of the helical worm 72 is rotary mounted to the alginate container 50; the helical worm 72 has a portion which runs outside of said alginate container 50. In addition, there is provided a tube 73 for housing the portion of the helical worm 72 which is outside of the alginate container 50, the tube 73 has a closed end 70, at which the other end of the helical worm 72 is rotary mounted; meanwhile the other end of the tube 73 is received in the alginate container 50. The tube 73 also has a downwardly facing opening 90 near to the closed end 70, this opening 90 defines the alginate dosing point 71 where dental alginate is dosed and received by a dentist.

Finally, there is provided a motor 74 as a further element of the transporting means, this motor 74 is preferably an electric step motor with a step resolution from about 1.0° to about 2.0°. As it can be noted, the electric step motor has a precise movement in order to dose only the dental alginate amount required for preparing an adequate mixture for taking a correct dental impression. The motor 74 acts as the rotating means that move the helical worm 72 inside the tube 73 and the alginate container 50.

Dental alginate is also homogenously distributed over the helical worm 72; for accomplishing this purpose, the automatic machine 10 includes distributing means, which in the first preferred embodiment, comprises: a first rotary roller 11 having a first plurality of radially protruding extensions 12; the first roller 11 is mounted inside the alginate container 50; a second rotary roller 13 having a second plurality of radially protruding extensions 14; this second roller 13 is also mounted inside said alginate container 50 and is laterally separated from the first rotary roller 11. When the machine 10 is in operation, the second rotary roller 13 rotates in opposite direction with respect to the first rotary roller 11. The distributing means also includes a double ribbon worm 15, which is mounted inside the alginate container 50 and centrally located therein; the double ribbon worm 15 is disposed between and under the first and second rotary rollers 11, 13.

The radially protruding extensions 12, 14 of the first and second rotary rollers 11, 13 are arranged in two pairs of diametrically opposite rows, of which, the extensions of one pair are larger than those extensions of the other pair. When the machine 10 is operating, a row of larger extensions of the first rotary roller 11 faces with a row of shorter extensions of the second rotary roller 13 at the center of the alginate container 50. The extensions 12, 14 have the form of straight blades with a rounded tip, and they have a length from about 1 inch (25.4 mm) to about 6 inches (152.4 mm). Other shapes for the extensions 12, 14 are also possible. The length difference between the extensions 12, 14 of the rotary rollers 11, 13 avoids dental alginate compression that may provoke an erroneous dosing of this substance.

As the first and second rollers 11, 13 rotate; the extensions 12, 14 push dental alginate to the center and towards the bottom of said alginate container 50, where dental alginate is received by the double ribbon worm 15, which homogenously distributes dental alginate over the transporting means, more specifically, over the helical worm 72. Homogenous distribution of dental alginate over the helical worm 72 is very important in order to dose an exact amount of this substance. In this regard, the double ribbon worm 15 allows accomplishing this requirement, inasmuch dental alginate is carefully deposited over the helical worm 72 from one side to the other side as the double ribbon worm 15 rotates.

As it can be anticipated, the double ribbon worm 15 and the first and second rotary rollers 11, 13 must be rotated, this movement is done by the aid of a micro-motor 19 represented by dashed lines and located under and outside the alginate container 50. The micro-motor 19 has an output shaft with a first gear 16, which is operatively coupled to a second gear 17 that is included at one end of the first rotary roller 11 and is located above of the first gear 16. The second gear 17 is also operatively coupled to a third gear 18 included at one end of the second rotary roller 13. In addition, there is provided a transmission belt 75 which connects the first rotary roller 11 with the double ribbon worm 15. Therefore, the rotational movement created by the micro-motor 19 is transmitted to the first rotary roller 11 via the first and second gears 16, 17, on the-other hand, the second gear 17 moves the third gear 18 which, in turn, moves the second rotary roller 13. Finally, the double ribbon worm 15 is moved by the transmission belt 75 as the first rotary roller 11 rotates.

The first and second rotary rollers 11, 13 as well as the double ribbon worm 15 are preferably made of polymeric materials, for example, ABS (acrylonitrile butadiene styrene) plastics. On the other hand, the helical worm 72 can be made of stainless steel or ABS plastics.

Now, it is important to mention that the control unit 80 is electrically connected to: i) the pump 30 and the valve 40 of the flowing means; ii) the motor 74 of the transporting means; and, iii) the micro-motor 19 of the distributing means. Therefore, when a user wishes to obtain water and dental alginate from the machine, he only has to operate said control unit 80, which, in turn, operates the pump 30 and the valve 40 in order to dose a predetermined amount of water from said water container 20 to the water dosing point 22. Then, said control unit 80 operates the micro-motor 19 in order to move dental alginate inside said alginate container 50 and homogenously distribute dental alginate over the helical worm 72 of the transporting means. Finally, the helical worm 72 carries a predetermined amount of dental alginate from the bottom of said alginate container 50 to the alginate dosing point 71.

Once the predetermined amount of alginate has been dosed, said control unit 80 changes the operating direction of the helical worm 72 in order to return any alginate amount remaining in the tube 73 to said alginate container 50. Preferably, when the electric motor 74 is a step motor, it rotates from about 3° to about 5° when changing the operating direction thereof.

Figure 8:
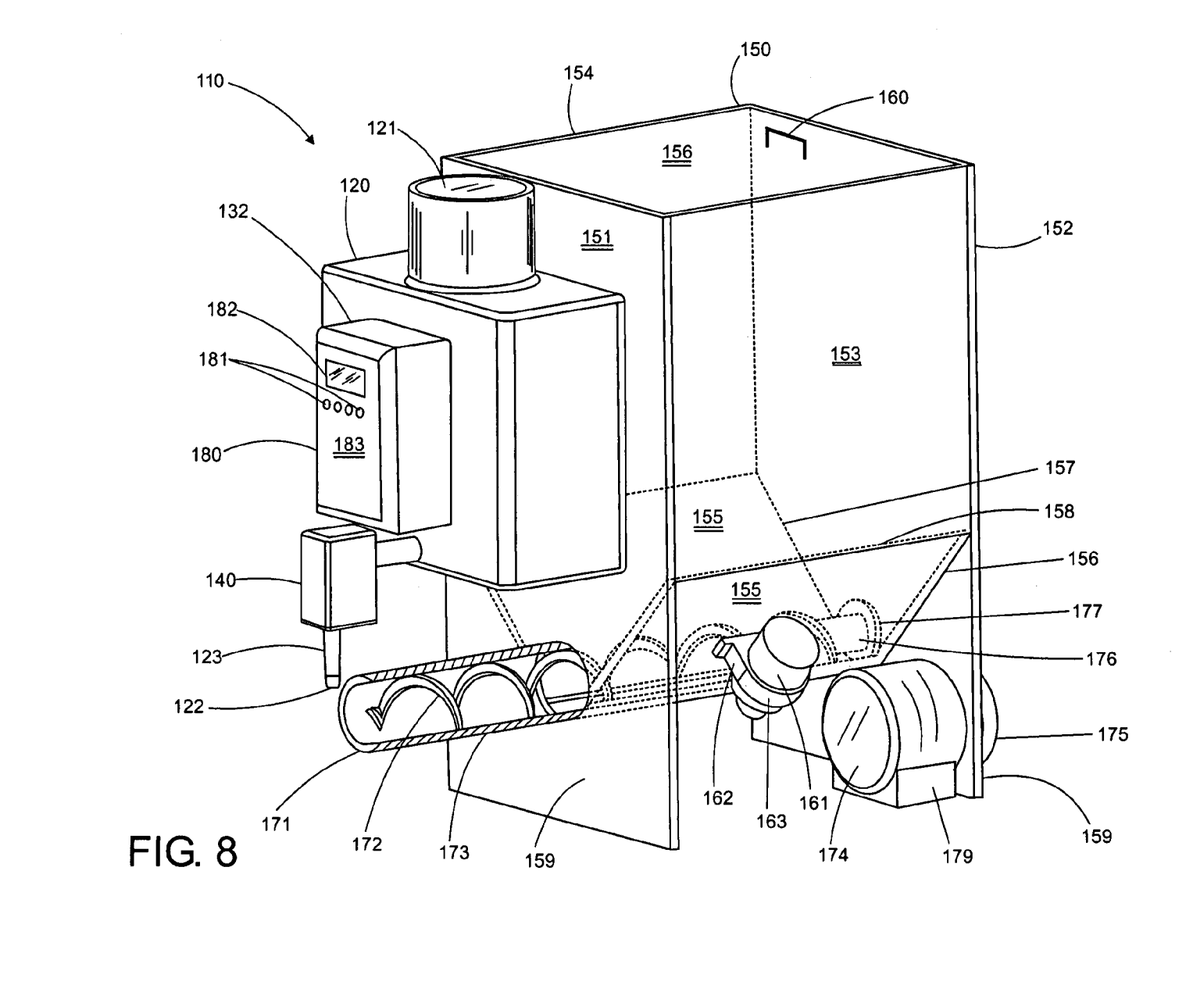
FIG. 8 is a perspective and fragmentary view of an automatic machine for dosing water and dental alginate, which is built in accordance with a second preferred embodiment of the present invention.
Figure 9:
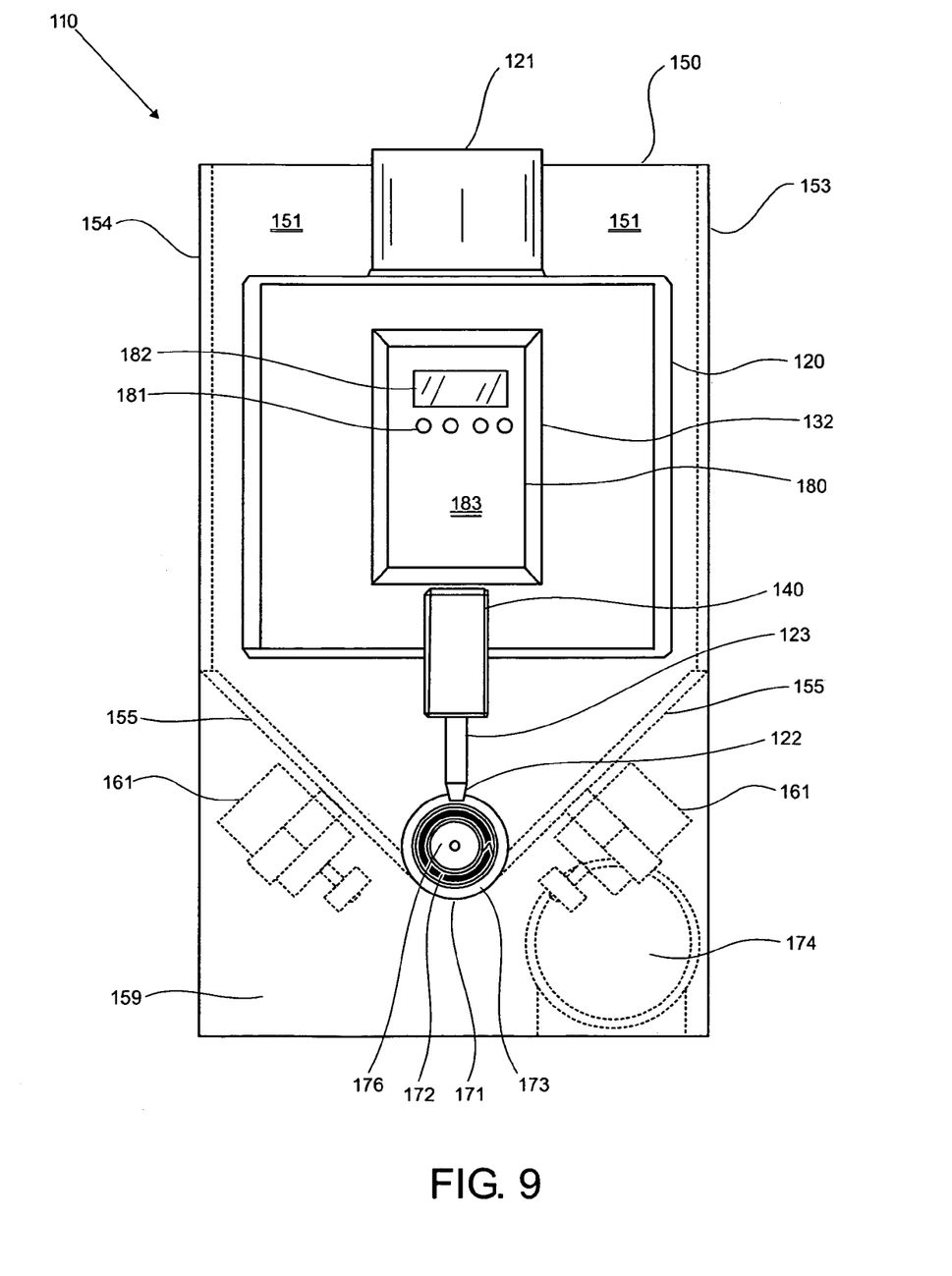
FIG. 9 is a front view of the automatic machine for dosing water and dental alginate shown in FIG. 8.
Figure 10:
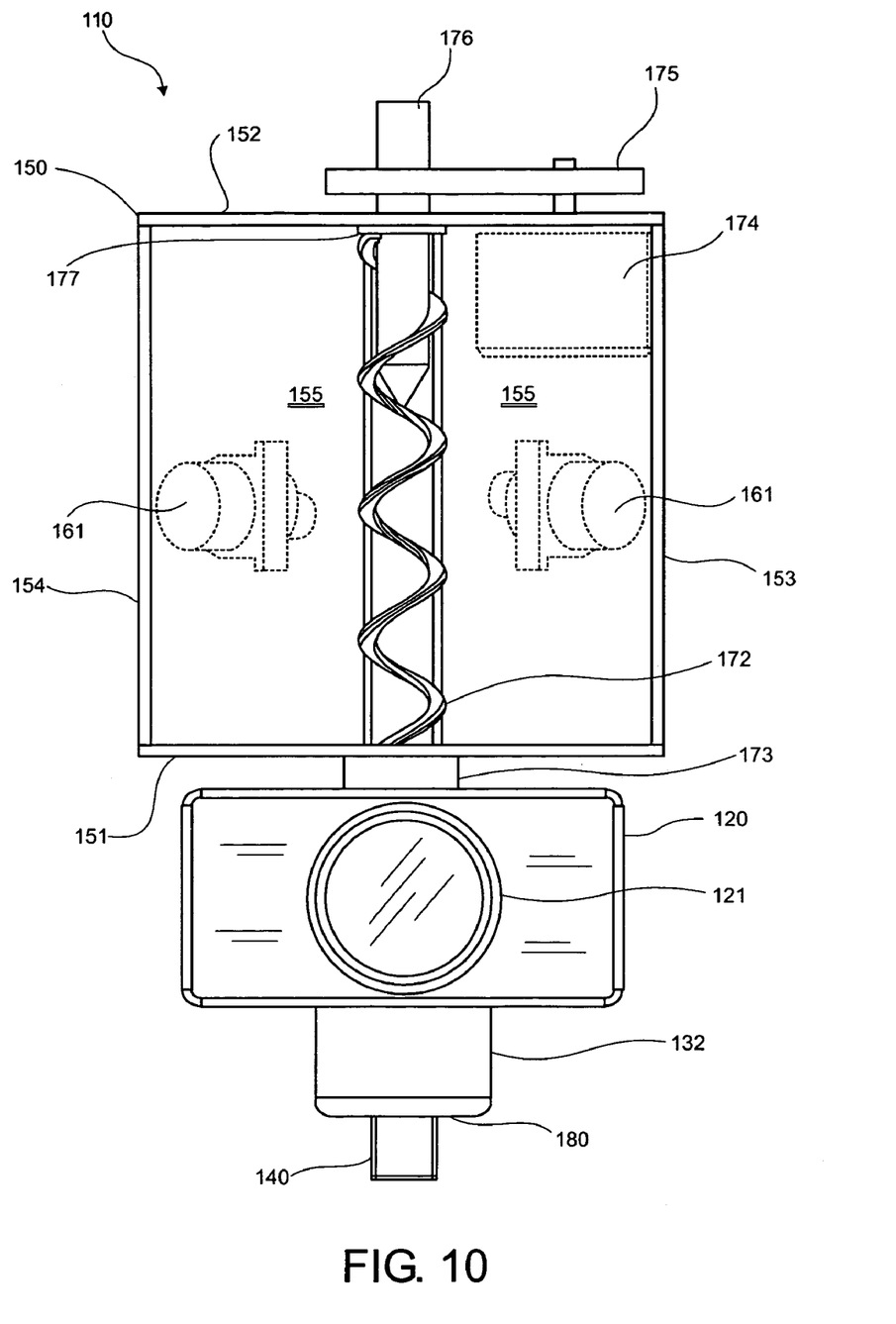
FIG. 10 is a top plan view of the automatic machine for dosing water and dental alginate shown in FIG. 8.

Now, reference is made to FIGS. 8 to 11 which show a second preferred embodiment, in which, similar components with respect to the first preferred embodiment are designated with similar numerals but having a "1" prefix added. In the second preferred embodiment vibrating means are used instead of the distributing means. FIGS. 8 to 10 of the appended drawings show an automatic machine for dosing water and dental alginate 110, built in accordance with the principles of a second preferred embodiment of this invention. The automatic machine 110 of this second preferred embodiment comprises a water container 120, preferably pressurized, in which water is stored; the water container 120 is pressurized by pressure means, that, in this second preferred embodiment, is an air pump 132 which supplies air to the inside of the water container 120, thus forming and air chamber above the surface of water. Preferably, the air pump 132 is a diaphragm type pump, such as those used in house aquariums.

To maintain the pressure inside the water container 120, the same includes a hermetic lid 121, which, in addition, can be removed in order to add water inside the water container 120 when the level of this liquid is lower than a minimum level.

In FIG. 8, it can be observed that the automatic machine 110 is provided with a valve 140 in flow connection with said water container 20. During operation of the automatic machine 110, the valve 140 allows water to flow from the water container 120 to a water dosing point 122. In this regard, the valve 140 is preferably an electrovalve and the water dosing point 122 is the output of a nozzle 123 being, of course, in flow connection with the valve 140. The elements 123 and 140 have the function of dosing the exact amount of water required by a user, in other words, they are calibrated in order to let flow a predetermined amount of water.

On the other hand, the automatic machine for dosing water and dental alginate 110 comprises a series of elements for handling and dosing the required amount of dental alginate.

With regard to the above, from FIGS. 8 to 10, it can be observed that the automatic machine 110 comprises an alginate container 150 having the form of a rectangular hopper with a front wall 151, a rear wall 152, two lateral walls 153, 154, a bottom 155 and a lid 156 closing the alginate container 150. The bottom 155 is formed by two sloping sections 157 and 158, each of them extending from the inferior edge of the lateral walls 153, 154 to the longitudinal middle line of the alginate container 150, where the sloping sections 157 and 158 join each other.

The lid 156 hermetically closes the alginate container 150 and is hingely connected thereto, if the level of alginate inside the alginate container 150 is lower than a minimum level, the user may add alginate therein opening the lid 156 with a handle 160 that is attached to the lid 156.

Moreover, with the purpose of constructing an automatic machine for dosing water and dental alginate 110 very compact in size, the front wall 151 and the rear wall 152 have each a vertical extension 159 formed integrally therewith and the water container 120 is joined to the front wall 151 of the alginate container 150. Each vertical extension 159 runs downwardly from the bottom 155 of the alginate container 150 in order to form supporting members for the automatic machine 110.

As it was mentioned, the alginate container 150 is preferably made of polyethylene, this polymer avoids alginate to be adhered on the internal walls of the alginate container 150, and therefore old alginate is never kept inside the alginate container 150.

The above disclosed form of the alginate container 150 and the preferred material used for its construction allow keeping and dosing dental alginate in optimal conditions. Preferably, alginate container 150 may store from about 1 pound (0.454 kg) to about 7 pounds (3.18 kg) of dental alginate, more preferably it may store about 5 pounds (2.28 kg), and this volume of the alginate container 150 allows a dentist to work for several weeks without refilling the alginate container 150.

The automatic machine for dosing water and dental alginate 110 is also provided with means for vibrating the alginate container 150, in the second preferred embodiment illustrated in FIGS. 8-10, the vibrating means comprises a pair of electric vibrator motors 161, each of them being in contact with the external surface of the bottom 155 of the alginate container 150. The electric vibrator motors 161 are symmetrically located on the external surface of the bottom 155, and each of them is put in contact thereto by means of a base 162 firmly attached to the alginate container 150; the base 162 includes a holder 163 surrounding the electric vibrator motor 161. In FIGS. 9 and 10, the electric vibrator motors 161 are represented in dashed lines, however, these figures allow to observe how such electric vibrator motors 161 are in contact with the bottom 155 of the alginate container 150.

Specifically, the vibrating means have the objective of moving alginate inside the alginate container 150, as well as, have the objective of bringing down residues of alginate adhered to the internal walls of the alginate container 150, if any. To accomplish such objectives, each of the electric vibrator motors 161 generates high frequency vibrations that are transmitted to dental alginate through the bottom 155 of the alginate container 150. In this regard, alginate may also be moved inside the alginate container 150 by means of a distributing mechanism operating inside the alginate container 150 as that included in the first preferred embodiment.

Alginate is transported from the bottom 155 of the alginate container 150 to an alginate dosing point 171 located outside the alginate container 150 by transporting means, which in the second embodiment, comprises: a helical worm 172 horizontally disposed along the bottom 155 of the alginate container 150 and rotary mounted thereto; the helical worm 172 has a portion running outside of the alginate container 150 and ending at the alginate dosing point 171. As another element of the transporting means; there is provided a tube 173 for housing the portion of the helical worm 172 which is outside of said alginate container 150; one end of the tube 173 is received in said alginate container 150. Finally, there is a motor 174 operatively connected to said helical worm 172 in order to rotate the same inside the alginate container 150 and the tube 173.

Preferably, the motor 174 is connected to the helical worm by means of a transmission belt 175 and is supported by a motor base 179 joined to the alginate container 150. In FIGS. 9 and 10 the motor 174 is represented by dashed lines and is preferably configured as an electric step motor with a step resolution from about 1.0° to about, 2.0°, and more preferably of 1.5°.

Figure 11:
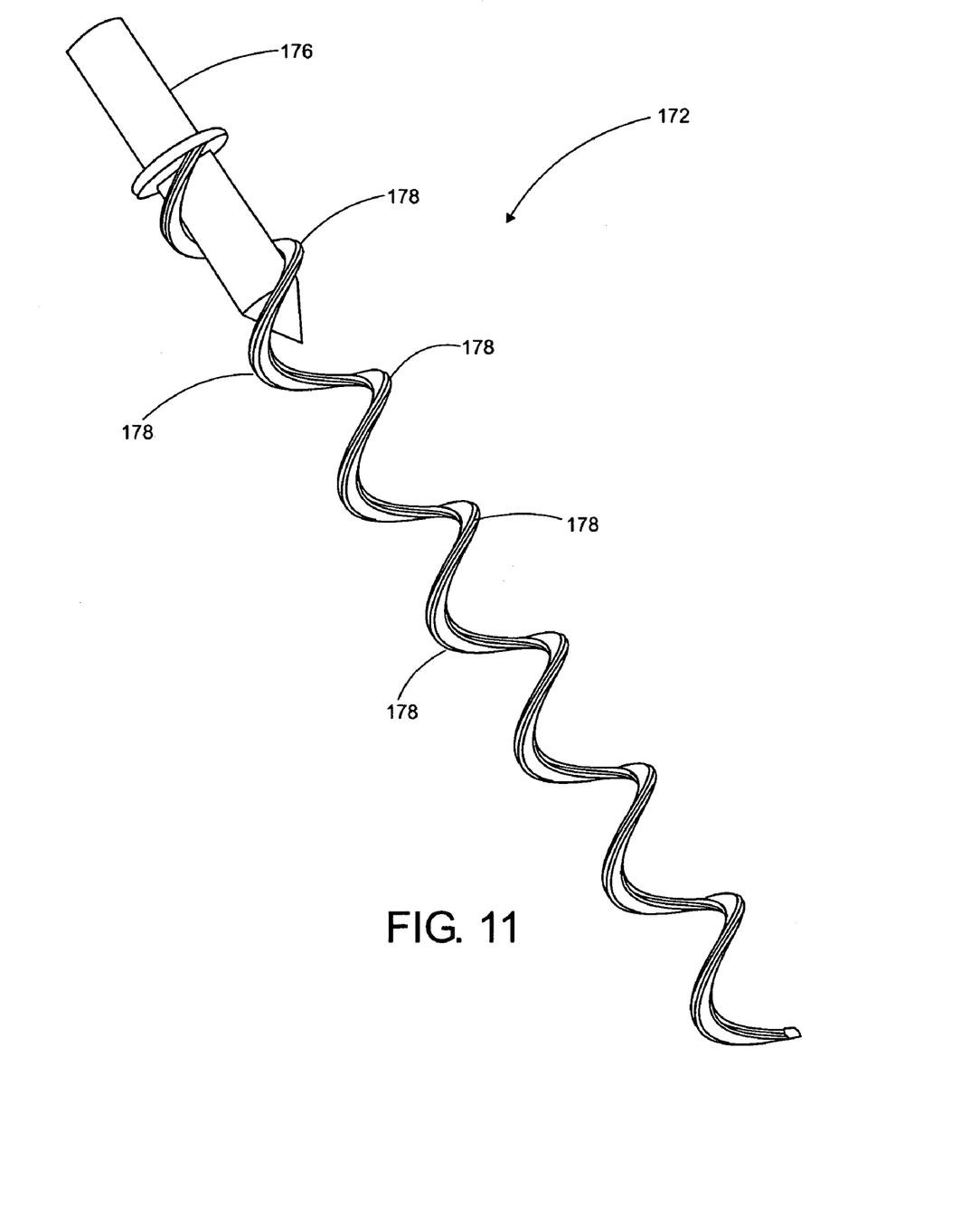
FIG. 11 is a perspective view of the helical worm which forms part of the transporting means included in the automatic machine for dosing water and dental alginate shown in FIG. 8.

For mounting the helical worm 172 to the alginate container 150, an end of the helical worm 172 is firmly joined to a rotary base 176 that is received in a bearing 177 disposed on the rear wall 152 of the alginate container 150, such rotary base 176 can be easily observed in FIG. 11, which shows a perspective view of the helical worm 172 provided with blades 178. In this regard, the blades of the helical worm 172 partially cover the cross section of the tube 173. This feature of the helical worm 172 along with the step resolution of the step motor allow to transport an exact amount of alginate from the alginate container 150 to the alginate dosing point 171 defined by the free end of the tube 173. In this second preferred embodiment, the alginate dosing point 171 is located under the water dosing point 122, thus, when the automatic machine 110 is in operation, a dentist may easily collect both substances in a separate vessel and mix them.

This configuration for the transporting means allow dentists to handle and dose alginate in the exact amounts for preparing an adequate gel. Other configurations for the transporting means may also be possible, such a conveyor belt which extracts and transports a predetermined volume of alginate powder from the alginate container 150, however, this solution is not so efficient as the arrangement of transporting means previously disclosed for the first or second embodiment.

In FIGS. 8-10, it can be observed that the automatic machine for dosing water and dental alginate 110 further comprises a control unit 180 electrically connected to: i) said valve 140, ii) the electric vibrator motors 161, and iii) the motor 174 of the transporting means. When the user wishes to obtain water an dental alginate, he only has to operate said control unit 180, which in turn opens and closes said valve 140 in order to dose a predetermined amount of water from said water container 120 to the water dosing point 122; then, said control unit 180 operates the electric vibrator motors 161 in order to move dental alginate inside said alginate container 150 and, immediately after and keeping in operation said electric vibrator motors 161, the control unit 180 operates the electric motor 174 that make the helical worm 172 to rotate inside the alginate container 150 in order to transport a predetermined amount of dental alginate from the bottom 155 of said alginate container 150 to the alginate dosing point 171.

Once the predetermined amount of alginate has been dosed, said control unit 180 stops the operation of the electric vibrator motors 161 and changes the operating direction of the motor 174, in order to return any alginate amount remaining in the tube 173 to the alginate container 150. This returning movement of electric motor 174 makes alginate to be lightly compacted inside the alginate container 150, this function of the automatic machine 110 has the object of not provoking an erroneous dose each time that the automatic machine 110 is put in operation. Preferably, when the motor 174 is an electric step motor, it rotates from about 3° to about 5° when changing the operating direction thereof.

In order to perform the controlled operations of the automatic machine 110, the control unit 180 comprises: a memory which stores dosing programs, each of them corresponding to a specific ratio between the amounts of water and dental alginate to be dosed; a control panel 183 having a plurality of keys 181, each of said keys 181 corresponding to a specific dosing program that the user may select; and, a display 182, which is in electrical connection to the keys and the memory, the display 182 shows the user the specific dosing program being performed by the automatic machine 110.

In an alternative embodiment of the invention, the memory of the control unit 80, 180 is programmable in order that the user may vary the amount of water to be dosed with respect to the amount of dental alginate. This feature for the memory implies an advantage for the user, inasmuch as he can use alginate of different manufactures. For dentists, it is well known that the properties of alginate vary from one producer to another.

In an alternative embodiment of the present invention which is not shown in the appended drawings, the automatic machine 10, 110 further comprises: a first sensor associated to said alginate container 50, 150 and being in electrical connection with said control unit 80, 180 the first sensor generating a first signal which is transmitted to said control unit 80, 180, which in turn indicates the user the alginate powder amount available inside said alginate container 50, 150. Likewise, in this alternative embodiment, the automatic machine 10, 110 comprises a second sensor associated to the water container 20, 120 and being in electrical connection with said control unit 80. 180, the second sensor generating a second signal which is transmitted to said control unit 80, 180, which, in turn, indicates the user the water amount available in said water container 20, 120. Therefore, if the level of water or dental alginate is lower than a minimum level, the control unit 80, 180 emits a visual or sound alarm.

In accordance with that previously described and as illustrated in the attached drawings, it may be seen that the automatic machine used for dosing water and dental alginate has been designed to handle and dose exact quantities of such substances, consequently, dentists save time and they will be sure of preparing an adequate mixture for taking dental impressions. The machine is compact in size and may handle alginate of different manufactures, so it will be obvious to any expert in this area that the embodiments described previously are only illustrative and not limit the invention, as there are numerous modifications that may be made, such as the form of the alginate container, the location of the vibrating means with respect to the alginate container, and others, without this altering the essential scope and function of the invention.

Even though some specific embodiments of this invention have been described and illustrated, we should emphasize that there are numerous modifications that may be made. Therefore, this invention should not be considered as restrictive, except for that which the prior art requires, and for the attached claims.

What is claimed is:

1. An automatic machine for dosing water and dental alginate, which comprises:
    a) a water container in which the water is stored:
    b) means for flowing the water from said container to a water dosing point;
    c) an alginate container in which the dental alginate is stored, said alginate container having a center and a bottom;
    d) means for transporting the dental alginate from the bottom of said alginate container to an alginate dosing point which is outside of said alginate container;
    e) means for distributing the dental alignate over said transporting means; wherein said distributing means comprises:
        a first rotary roller having a first plurality of radially protruding extensions, said first roller being mounted inside said alginate container and rotating in a first direction;
        a second rotary roller having a second plurality of radially protruding extensions, said second roller being mounted inside said alginate container and being laterally separated from said first rotary roller; wherein said second rotary roller rotates in a second direction opposite to the first direction;
        a double ribbon worm mounted inside said alginate container and centrally located therein, said double ribbon worm being disposed between and under said first and second rotary rollers; and,
        means for rotating said double ribbon worn and said first and second rotary rollers, whereby, as said first and second rollers rotate, said extensions thereof move the dental alginate to the center and toward the bottom of said alginate container, where the dental alginate is received by said double ribbon worn, which homogenously distributes the dental alginate over said transporting means; and
    f) a control unit being electrically connected to: i) said flowing means, ii) said transporting means, and iii) said distributing means;
    wherein said control unit operates said flowing means in order to dose a predetermined amount of water from said water container to the water dosing point; then said control unit operates said distributing means in order to move the dental alginate inside said alginate container and homogenously distribute the dental alginate over said transporting means, said transporting means are also operated by said control unit in order to carry a predetermined amount of the dental alginate from the bottom of said alginate container to the alginate dosing point, and once the predetermined amount, of the alginate has been dosed, said control unit operates said transporting means in order to return any amount of the alginate remaining in said transporting means to said alginate container.

2. An automatic machine for dosing water and dental alginate, according to claim 1, wherein said rotating means is a micro-motor.

3. An automatic machine for dosing water and dental alginate, according to claim 1, wherein said radially protruding extensions of the first and second rotary rollers are arranged in two pairs of diametrically opposites rows, of which the extensions of one pair are larger than the extensions of the other pair, so that, when the machine is operating, a row of larger extensions of said first rotating roller faces with a row of shorter extensions of said second rotating roller.

4. An automatic machine for dosing water and dental alginate, according to the claim 1, wherein said radially protruding extensions to have the form of straight blades with a rounded tip.

5. An automatic machine for dosing water and dental alginate, according to claim 4, wherein said radially protruding extensions have a length of about 1 inch to about 6 miles.

6. An automatic machine for dosing water and dental alginate, according to claim 1, wherein said control unit comprises:
    a memory which stores dosing programs, each program corresponding to a specific ratio between the amounts of the water and the dental alginate to be dosed;
    a control panel having a plurality of keys, each of said keys corresponding to a specific dosing program that can be selected; and,
    a display, which is in electrical connection to the keys and to the memory, the display showing the specific dosing program being performed by the automatic machine.

7. An automatic machine for dosing water and dental alginate, according to claim 6, wherein said memory of said control unit is programmable in order vary the amount of the water to be dosed with respect to the amount of the dental alginate.

8. An automatic machine for dosing water and dental alginate, according to 1, wherein the automatic machine further comprises:
    g) a first sensor associated to said alginate container and being electrical connected with said control unit, said first sensor generating a first signal which is transmitted to said control unit in order to indicate the alginate amount available inside said alginate container; and,
    a second sensor associated to the water container and being in electrical connection with said control unit, said second sensor generating a second signal which is transmitted to said control unit in order to indicate the water amount in said container;
    so that, if the level of the water or the dental alginate is lower than a minimum level, said control unit emits a visual or sound alarm.

9. An automatic machine for dosing water and dental alginate, according to claim 1, wherein the alginate dosing point and the water dosing point are disposed one next to the other.

10. An automatic machine for dosing water and dental alginate, according to claim 1, wherein said flowing means comprises:
    a pump being in flow connection with said water container; and
    a valve being in flow connection with said pump and having an output;
    whereby, the water can flow from said water container to the water dosing point through said pump and said valve when said control unit is in operation.

11. An automatic machine for dosing water and dental alginate, according to claim 10, wherein said valve is an electrovalve having a hose provided with two ends, said first end being connected to the output of said valve and said second end being a free end that defines the dosing point of the water.

12. An automatic machine for dosing water and dental alginate, according to claim 1, wherein said transporting means comprises:

a helical worn horizontally disposed along the bottom of said alginate container, said helical worn having first and second ends, the first end of said helical worn being rotatably mounted to said alginate container; said helical worn having a portion which runs outside of said alginate container;

a tube for housing the portion of said helical worn that is outside of said alginate container, said tube having a closed end, wherein the second end of said helical worn is rotatably mounted, the tube also having a downwardly facing opening near to the closed end, the opening defining the alginate dosing point where the dental alginate is dosed; and means for rotating said helical worn inside said alginate container and said tube.

13. An automatic machine for dosing water and dental alginate, according to claim 12, wherein said rotating means is an electric step motor having a step resolution from about 1.0° to about 2.0°.

* * * * *